United States Patent [19]

Tanaka et al.

[11] Patent Number: 5,112,454
[45] Date of Patent: May 12, 1992

[54] ION CONCENTRATION-MEASURING METHOD

[75] Inventors: Yasuji Tanaka, Tochigi; Akiko Tanaka, Ootawara, both of Japan

[73] Assignee: Kabushiki Kaisha Toshiba, Kawasaki, Japan

[21] Appl. No.: 484,431

[22] Filed: Feb. 16, 1990

Related U.S. Application Data

[63] Continuation of Ser. No. 273,725, Nov. 18, 1988, abandoned, which is a continuation of Ser. No. 60,677, Jun. 11, 1987, abandoned.

[30] Foreign Application Priority Data

Jun. 16, 1986 [JP] Japan .................. 61-138305

[51] Int. Cl.⁵ .................. G01N 27/26; G01N 27/333
[52] U.S. Cl. .................. 204/153.1; 204/153.13; 204/153.15; 204/400; 204/407; 204/409; 204/411; 204/416
[58] Field of Search ......... 204/401, 411, 1 T, 153.1, 204/400, 153.13, 153.15, 407, 409, 416; 73/1 R

[56] References Cited

U.S. PATENT DOCUMENTS

| | | | |
|---|---|---|---|
| 3,556,950 | 1/1971 | Dahms | 204/1 T |
| 4,043,756 | 8/1977 | Sommervold | 23/230 R |
| 4,109,505 | 8/1978 | Clark et al. | 73/1 R |
| 4,512,852 | 4/1985 | Tsuboshima et al. | 204/1 T |
| 4,600,494 | 7/1986 | Bromberg et al. | 204/401 |
| 4,627,893 | 12/1986 | Cormier et al. | 204/1 T |
| 4,647,362 | 3/1987 | Watanabe | 204/411 |
| 4,668,346 | 5/1987 | Entwistle | 204/1 T |

FOREIGN PATENT DOCUMENTS

3220327 12/1982 Fed. Rep. of Germany.

Primary Examiner—T. Tung
Attorney, Agent, or Firm—Oblon, Spivak, McClelland, Maier & Neustadt

[57] ABSTRACT

The electromotive force of a standard liquid for correction is measured. Both before and after this measurement, the electromotive force of a reference liquid is measured at least once. A calibration curve is prepared based on the resultant data. The calibration curve is used to convert the electromotive force difference between a test liquid (the ion concentration of which is to be measured) and the reference liquid. Both before and after the measurement of the electromotive force of the test liquid, the electromotive force of the reference liquid is measured at least once. By so doing, the electromotive force difference between the test liquid and the reference liquid is obtained. The ion concentration of the test liquid can be detected accurately by plotting the electromotive force difference against the calibration curve.

4 Claims, 11 Drawing Sheets

ION CONCENTRATION-MEASURING METHOD

This application is a continuation of application Ser. No. 07/273,725, filed on Nov. 18, 1988, now abandoned, which is a continuation of Ser. No. 060,677, filed Jun. 11, 1987, now abandoned.

BACKGROUND OF THE INVENTION

The present invention relates to a method for measuring the electrolytic ion concentration of a sample liquid (e.g., the body fluid of an organism) by use of an automatic chemical analyzer, and to a system for using the method.

With a conventional method, the concentration of ions (such as Na, K, and Cl ions) in the body fluid of an organism is detected as follows. A liquid, such as the body fluid, the ion concentration of which is to be detected, will be referred to as a test liquid hereinafter. The electromotive force of a test liquid with an unknown ion concentration is measured by use of an ion-selective electrode. To correct the electromotive force measured, a reference liquid with a known ion concentration is used. More specifically, the electromotive force of this reference liquid is measured once, before or after the electromotive force of the test liquid is measured. The difference between the electromotive force of the test liquid and that of the reference liquid is calculated. By plotting the calculated difference against a calibration curve, which is prepared beforehand, the ion concentration corresponding to the difference is obtained. In the conventional method, however, the electromotive force of the reference liquid is measured only once, before or after the electromotive force of the test liquid is measured, or before or after the electromotive force of a standard liquid for correction is measured during the process of preparing the calibration curve. Therefore, there may be a delay in the response of the ion-selective electrode or an abrupt drift in the electromotive force, due to changes in the ambient temperature of the ion-selective electrode. Due to these adverse effects, the electromotive force of the reference liquid and that of the test liquid cannot be measured very reliably. Accordingly, it is very difficult to accurately detect the ion concentration of the test liquid. In order to eliminate the adverse effects noted above, the temperature of the ion-selective electrode must be strictly maintained at a constant value.

As can be seen from the foregoing, in order to accurately detect the ion concentration of the test liquid, it is very important to prepare the calibration curve without adverse effects caused by changes in the ambient temperature of the ion-selective electrode. It is also important to accurately measure the electromotive force of the reference liquid as well as the electromotive force of the test liquid.

SUMMARY OF THE INVENTION

The object of the present invention is to provide an ion concentration-measuring method and a system therefor, which enable an accurate calibration curve to be prepared and used in an automatic chemical analyzer, and which ensure accurate detection of the ion concentration of a test liquid by accurately measuring the electromotive force of a reference liquid.

According to one aspect of the present invention, there is provided an ion concentration-measuring method which can accurately detect the ion concentration of a test liquid by measuring the electromotive force of a standard liquid for correction at least once, measuring the electromotive force of a reference liquid with a known ion concentration at least once, before and after the measurement of the electromotive force of the standard liquid for correction, preparing a calibration curve on the basis of the electromotive force differences between the standard liquid for correction and the reference liquid, measuring the electromotive force of the test liquid with an unknown ion concentration once, measuring the electromotive force of the reference liquid at least once before and after the measurement of the electromotive force of the test liquid, and plotting, against the calibration curve, a value representing the difference between the measured electromotive force of the test liquid and that of the reference liquid.

According to another aspect of the present invention, there is provided an ion concentration-measuring system comprising means for measuring the electromotive force of a standard liquid for correction at least once, means for measuring the electromotive force of a reference liquid with a known ion concentration at least once, before and after the measurement of the electromotive force of the standard liquid for correction., means for preparing a calibration curve on the basis of the electromotive force differences between the standard liquid for correction and the reference liquid, means for measuring the electromotive force of the test liquid with an unknown ion concentration once, means for measuring the electromotive force of the reference liquid at least once before and after the measurement of the electromotive force of the test liquid, and means for providing the ion concentration of the test liquid by plotting, against the calibration curve, the difference between the measured electromotive force of the test liquid and that of the reference liquid.

DETAILED DESCRIPTION OF THE PREFERRED EMBODIMENTS

One embodiment of the present invention will be described, with reference to the accompanying drawings.

Figure 1:
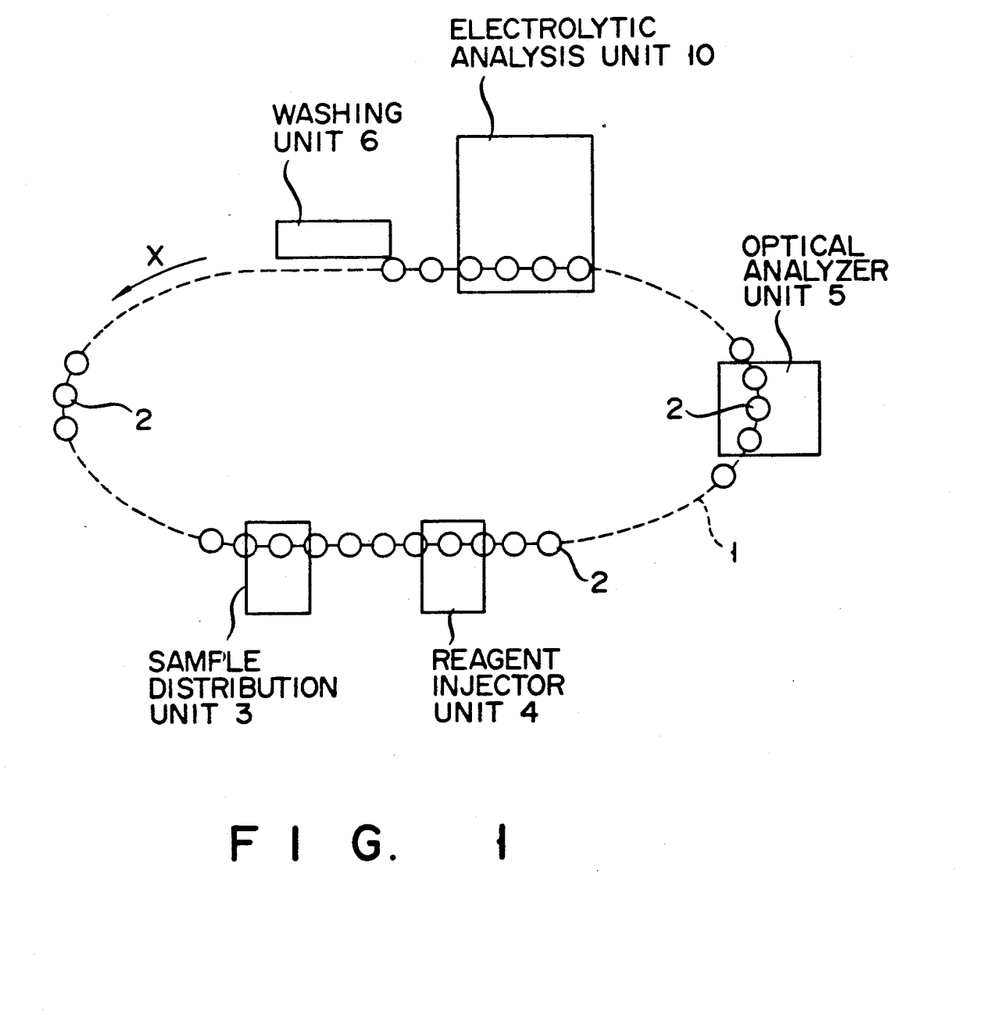
FIG. 1 is a view illustrating the construction of an automatic chemical analyzer used in the method of the present invention.

FIG. 1 is a view schematically illustrating an automatic chemical analyzer which is used in the method of the present invention. Referring to FIG. 1, a large number of test tubes 2 are successively transferred along endless reaction line 1 in the X direction. A sample, e.g., a blood serum, is distributed into the test tubes denoted by reference symbols 2b (see FIG. 2), by use of sample distribution unit 3 with a sampling nozzle. A reference liquid is distributed into the test tubes denoted by reference symbols 2a, 2c and 2d. All test tubes 2 (namely, the ones denoted by 2a–2d) are successively transferred to reagent injector unit 4. By means of a reagent supply nozzle of this unit, a predetermined reagent is distributed into each test tube 2, thereby mixing the sample and reagent with each other to produce a chemical reaction. Thereafter, the mixture is transferred to optical analyzer unit 5, where the mixture is subjected to a color test. After the color test, test tubes 2a–2d are transferred to electrolytic analysis unit 10 (which will be described in detail below), and finally to washing unit 6. All test tubes 2 are washed and cleaned by washing unit 6.

Figure 2:
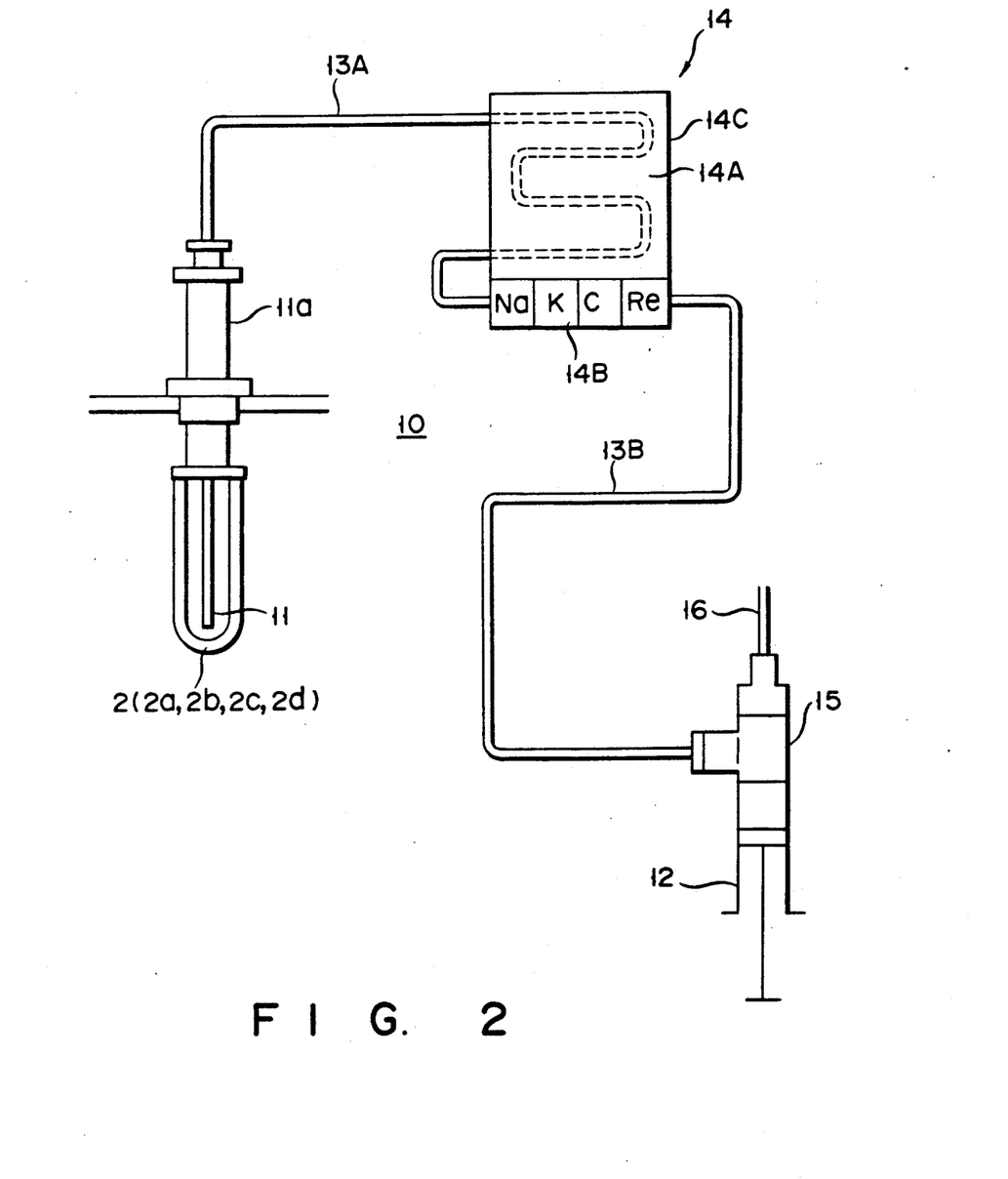
FIG. 2 is an explanatory view of an electrolyte-analyzing device.

As is shown in FIG. 2, electrolytic analysis unit 10 is formed by: suction nozzle 11, arranged along reaction line 1, for sucking the liquid from each test tube 2; suction pump 12; tubes 13A and 13B for connecting suction nozzle 11 and suction pump 12 to each other; and electrode device 14 located between tubes 13A and 13B. Suction nozzle 11 is provided with vertically movable mechanism 11a, used for sucking liquids from a certain test tubes 2 selected among those moving along response line 1. Electrode device 14 includes: heat block 14A around which tube 13A is wound; electrode section 14B through which the test liquid in tube 13A is made to pass for measuring electrolytes by use of an ion-selective electrode; and heat-retaining case 14C for containing heat block 14A and electrode section 14B. Three-way cock 15 is located between pump 12 and tube 13b, for selecting either the liquid suction mode or the liquid discharge mode. An outlet port of three-way cock 15 is connected to drain tube 16.

Figure 3:
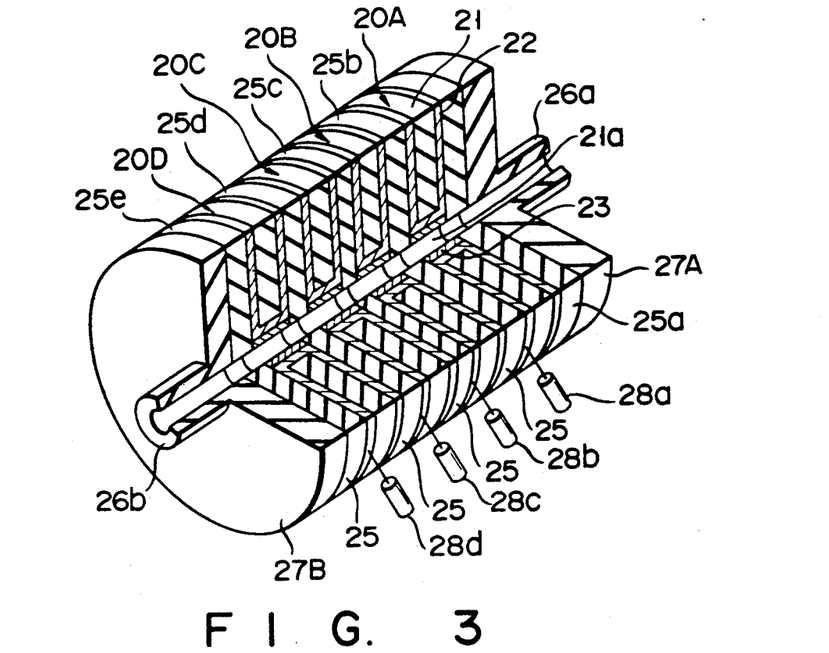
FIG. 3 is a partially-sectional, perspective view of an ion-selective electrode device used in the present invention.

FIG. 3 shows the construction of electrode section 14B. As shown, electrode section 14B includes four electrode units 20A–20D. Electrode unit 20A is formed by: discoid member 21 made of a thermally and electrically insulating material and having a small opening in the center; metal layers 22 formed on both sides of discoid member 21 and on the inner wall in the small opening 21a; and ion-sensitive layer 23 formed on that part of metal layer 22 which is located in the small opening 21a. The other electrode units 20B–20D have similar constructions. These four electrode units 20A–20D are combined with five thermal and electrical insulating plates 25a–25e, each having a small opening with the same diameter as the opening of electrode units 20A–20D. More specifically, four electrode units 20A–20D and five plates 25a–25e are alternately stacked in such a manner that each electrode unit 20A–20D is sandwiched by two of the plates 25a–25e, and that the openings of electrodes units 20A–20D and those of plates 25a–25e are aligned with one another. Electrode units 20A–20D and plates 25a–25e are joined with one another by clamping the resultant structure from both ends. Two holding plates 27A and 27B, formed of a thermally and electrically insulating material, are located at the respective ends of the structure. Among the four electrode units 20A–20D, the one denoted by 20A serves as a reference electrode, and the ones denoted by 20B–20D serve as ion-selective electrodes for selectively detecting ions, such as Na, K, and Cl ions, respectively. Reference electrode 20A and ion-selective electrodes 20B–20D serve as heat-insulating members as well, when they are used in practice. Therefore, they prevent the temperature of the sample liquid from dropping at the time of ion detection, thereby enabling the measurement to be made at a constant temperature.

Figure 4:
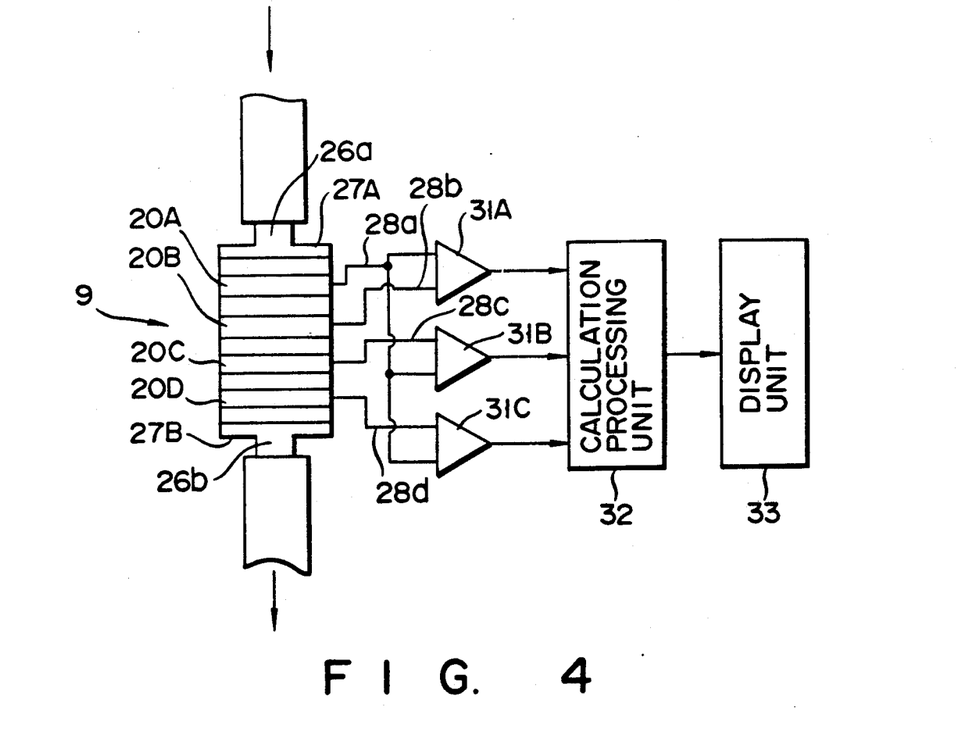
FIG. 4 is a block diagram of circuits connected to the electrode device.

Such a circuit as is shown in FIG. 4 is connected to reference electrode 20A and ion-selective electrodes 20B–20D. The circuit comprises: amplifiers 31A–31C which receive the electromotive force derived from electrodes 20A–20D through lead wires 28a–28d and which produce a voltage corresponding to the difference between the electromotive force of reference electrode 20A and that of the other electrodes 20B–20C; calculation processing unit 32 for calculating the ion concentration on the basis of the measured electromotive force and the calibration curve prepared beforehand; and display unit 33. Calculation processing unit 32 includes an A/D converter and a microcomputer. After A/D converting the outputs of amplifiers 31A–31C, calculation processing unit 32 detects the ion concentration on the basis of the electromotive force of the test liquid and the calibration curve prepared beforehand. Display unit 33 displays the ion concentration calculated by calculation processing unit 32.

Figure 5A:
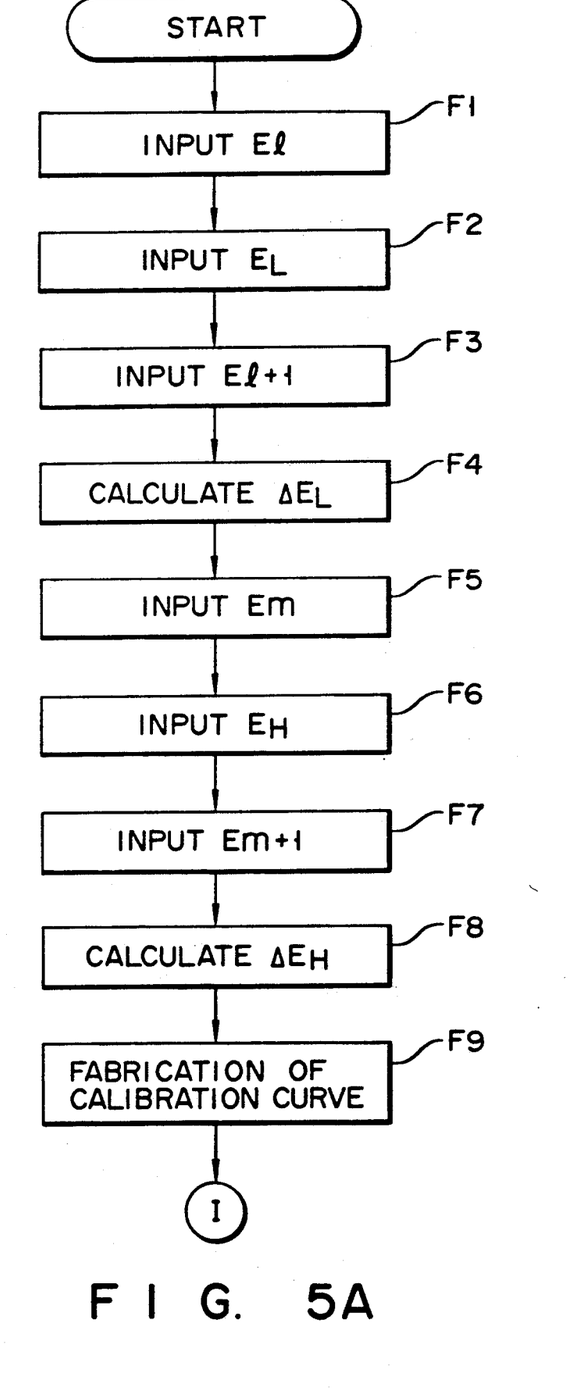
FIG. 5A is a flow chart for illustrating how a calibration curve is prepared.
Figure 5B:
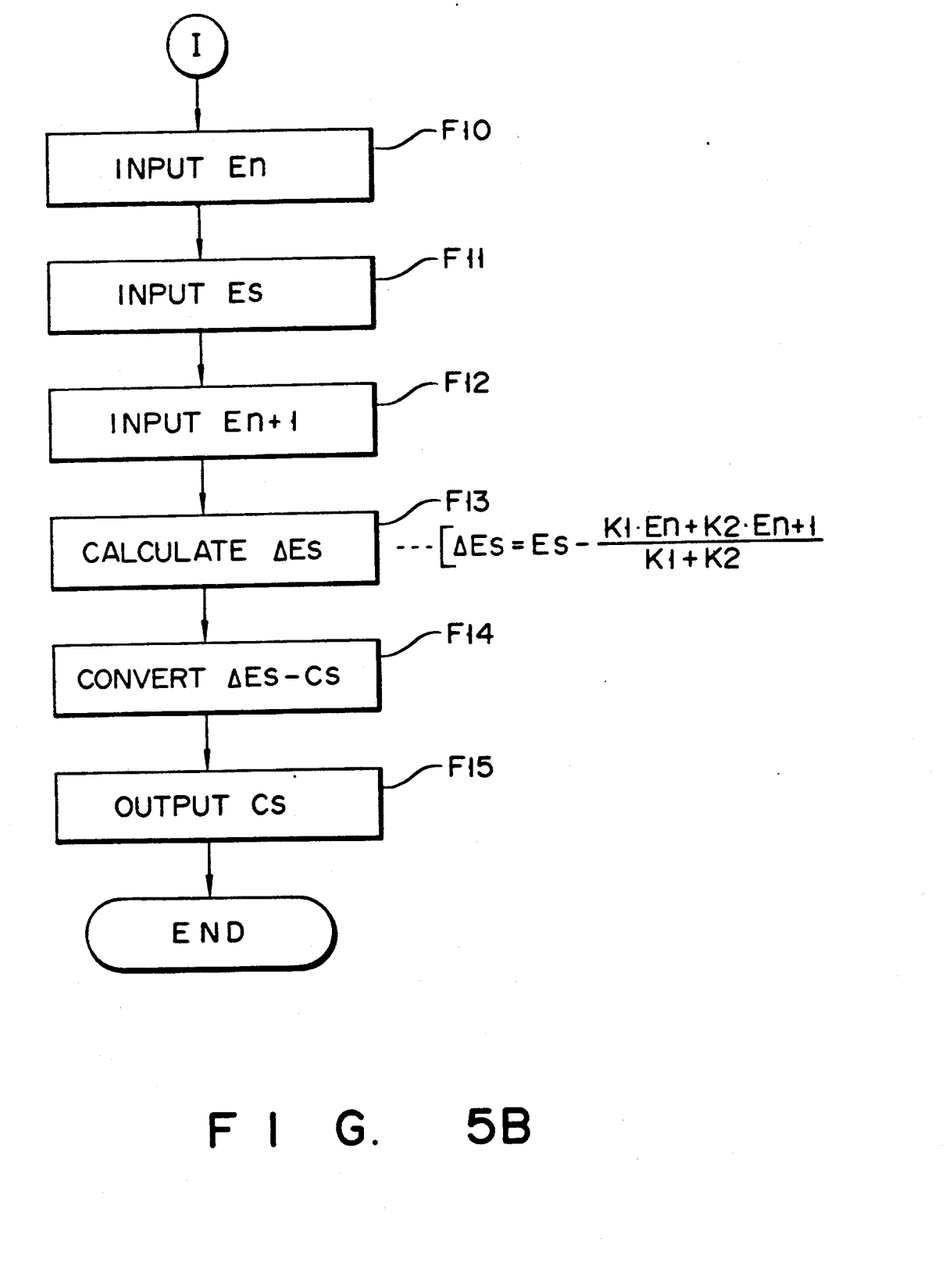
FIG. 5B is a flow chart for illustrating how an ion concentration is detected.

A description may now be given of how the ion concentration measurement proceeds under the control of the microcomputer, with reference to the flow charts shown in FIGS. 5A and 5B.

Before measuring the electromotive force of a sample of a test liquid, such as a blood serum, a calibration curve is prepared according to the flow chart shown in FIG. 5A. At this time, the electromotive force of a known low-concentration standard liquid (calibrator L) and that of a known high-concentration standard liquid (calibrator H) are measured in steps F2 and F6, respectively. Before and after the measurement of the electromotive force of each standard liquid, i.e., in steps F1 and F3 and steps F5 and F7, the electromotive forces of reference liquids with known ion-concentration corresponding to the two standard liquids are measured. In steps F4 and F8, electromotive force differences $\Delta EL$ and $\Delta EH$ between the two standard liquids and the corresponding reference liquids are calculated, respectively. The electromotive forces of the standard and reference liquids may be measured an increased number of times, in accordance with the necessity.

Figure 6:
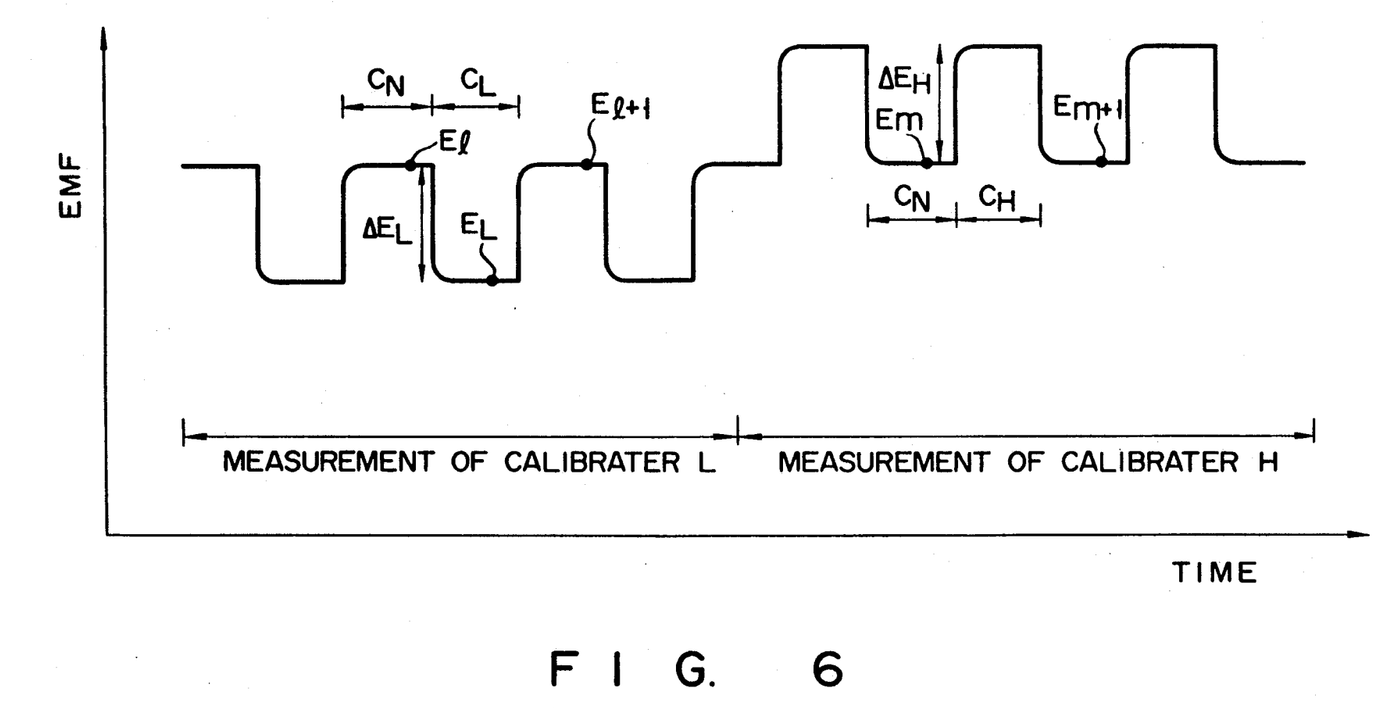
FIG. 6 is a waveform chart of the electromotive force obtained when the calibration curve is prepared.

FIG. 6 illustrates the waveform of the output voltage of the ion-selective electrodes, which is obtained by performing the measurement process shown in FIG. 5A. As can be seen from FIG. 6, if the electromotive forces of the reference liquids are detected at time points El and Em and time points El+1 and Em+1 (time points El and Em are before the measurement of the electromotive force of the standard liquids, and time points El+1 and Em+1 are after this measurement), it is possible to obtain both ion concentrations CL and CH (CL corresponds to electromotive force difference $\Delta EL$ between the low-concentration standard liquid and the related reference liquid, and CH corresponds to electromotive force difference $\Delta EH$ between the high-concentration standard liquid and the related reference liquid).

Ion concentration C and electromotive force E, measured by use of an ion-selective electrode, have the following relationship:

$$E = E0 + (RT/nF)\ln fC$$

where E0 represents an electromotive force determined when the temperature is constant, R represents the gas constant of a test liquid, T represents an absolute temperature, n represents the valence of ions to be measured, F represents a Faraday constant, and f represents an ion activity coefficient.

The ion activity coefficient f can be expressed as a function of the number of ions existing in a unit volume (i.e., ion strength). Therefore, if reference, standard, and test liquids are diluted with reagents and their ion strengths are maintained at constant values, then ion activity coefficient f can be also kept at a constant value. For this reason, ion concentration C can be calculated on the basis of measured electromotive force E.

Figure 7:
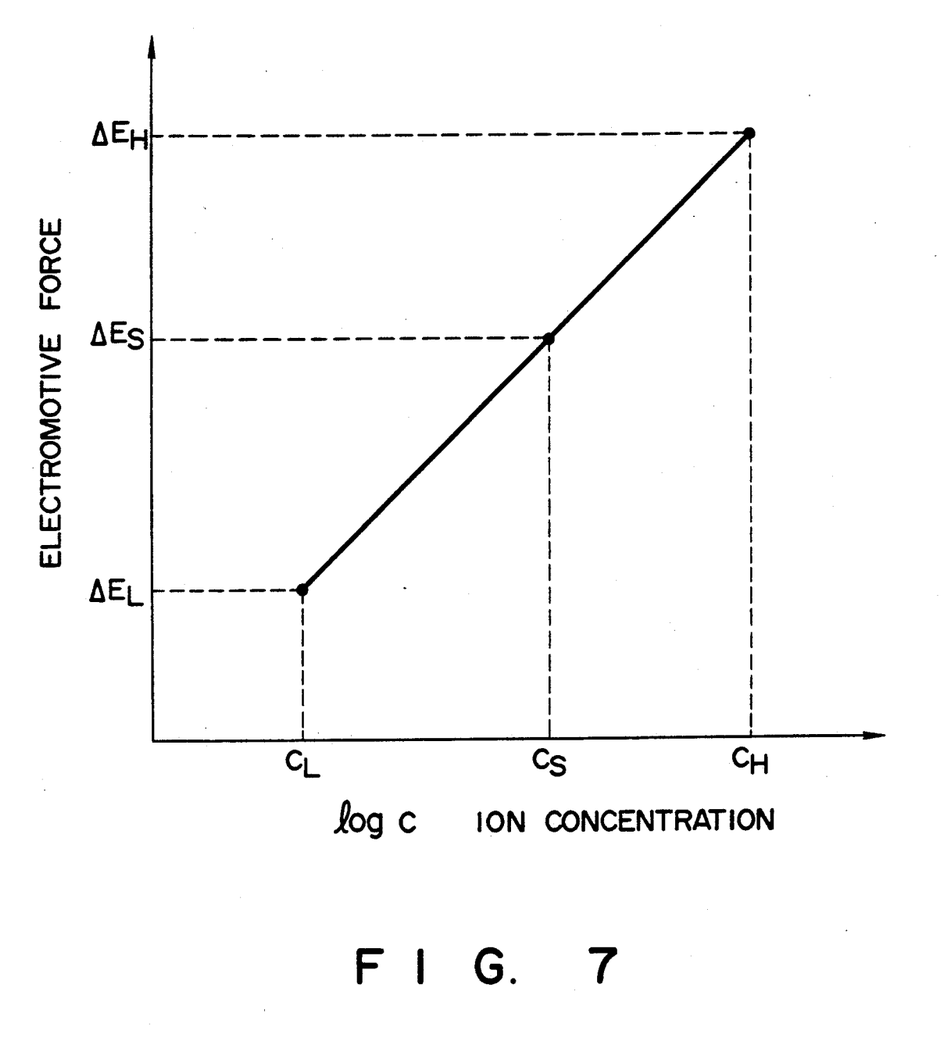
FIG. 7 is an example of the calibration curve.

On the basis of results of the measurement mentioned above, a calibration curve, by which ion concentration Cs corresponding to electromotive force difference $\Delta$Es between the test and reference liquids can be obtained, is prepared in step F9, as shown in FIG. 7.

Figure 8:
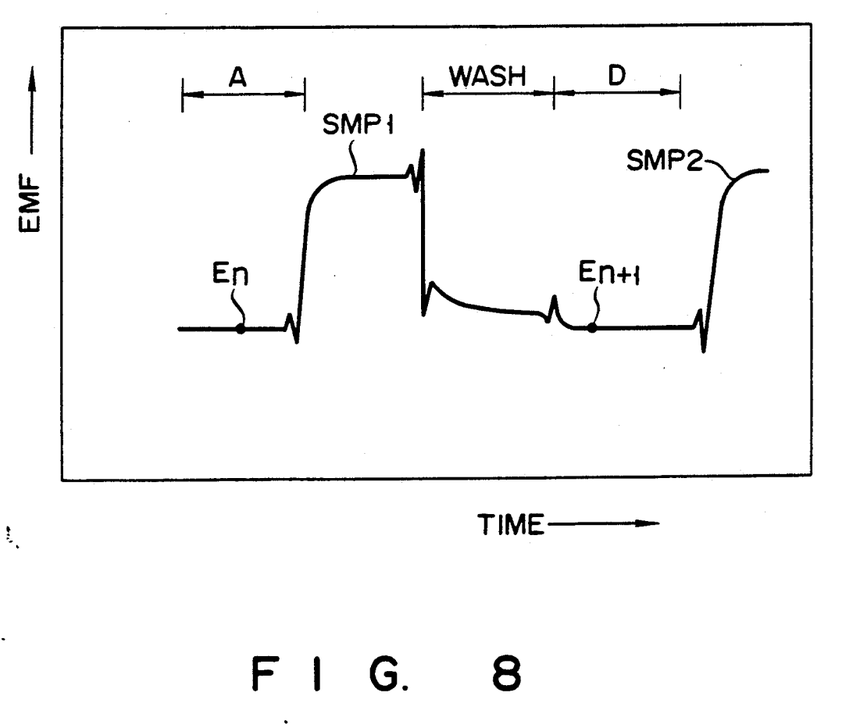
FIG. 8 is a waveform chart of the electromotive force obtained when the test liquid is measured.

After the preparation of this calibration curve, a sample measurement is made with respect to a liquid to be measured, such as a blood serum. As is shown in FIGS. 5B and 8, electromotive force difference $\Delta$Es is calculated on the basis of electromotive forces En, En+1, and Es. Specifically, the electromotive force of the reference liquid is measured before and after the electromotive force of test liquid SMP1 (FIG. 8) is measured in step F11, i.e., the electromotive force of the reference liquid is measured in step F10 (the time point indicated by En in FIG. 8) and in step F12 (the time point indicated by En+1 in FIG. 8). Thereafter, in step F13, electromotive force difference $\Delta$Es between the reference liquid and the test liquid is calculated, using the following formula:

$$\Delta Es = Es - (K1 \cdot En + K2 \cdot En + 1)/(K1 + K2)$$

where Es represents the electromotive force of the test liquid, En represents the electromotive force of the reference liquid measured before the sample measurement, En+1 represents the electromotive force of the reference liquid measured after the sample measurement. Constants K1 and K2, used in the above formula, are values experimentally determined on the basis of the response characteristics of each ion-selective electrode. Electromotive forces En and En+1, which are measured before and after the sample measurement, are weighted by constants K1 and K2, thereby calculating optimal electromotive forces. More specifically, in the case of Cl ions, the values of K1 and K2 are determined to be 0.5 and 0.5, respectively. If they are determined to be 1.0 and 1.0, respectively, then a mean of the electromotive forces of the reference liquid will be obtained. Incidentally, in FIG. 8, symbols A and D are used to indicate the reference liquids that will be described in detail with reference to FIGS. 9A-9F.

In the manner described above, the electromotive force of a reference liquid is measured at a plurality of time points, e.g., before and after the sample measurement, and electromotive force difference $\Delta$Es of the sample is calculated on the basis of the measured values. It is, therefore, possible to eliminate adverse effects caused when the temperature of the reference liquid changes with time, such as drift caused by a temperature rise of the reference liquid. It is also possible to correct errors which may be caused by a delay in the response of the ion-selective electrodes.

In the embodiment described above, the electromotive force of the reference liquid is measured once, both before and after the sample measurement. However, the present invention is not limited to this. The electromotive force of the reference liquid may be measured twice or more times, before and after the sample measurement. If the electromotive force is measured in this way, the average and the median of the measured values are calculated. In summary, in the present invention, the electromotive force of the reference liquid is measured a plurality of times, and on the basis of such measurement, the electromotive force of the test liquid is calculated. Therefore, the calculated electromotive force is very reliable. In accordance with the number of times of measurement, constants K1 and K2 may be replaced with K3 and K4, respectively. The values of these constants can be determined arbitrarily each time.

The ion concentration corresponding to electromotive force difference $\Delta$Es is obtained in step F14, on the basis of the calibration curve (FIG. 7) prepared beforehand. In step F15, the value of the ion concentration is displayed on display unit 33.

The operation of the subject apparatus will now be described.

A sample to be subjected to electrolytic analysis, a reference liquid and a reagent are selectively supplied into test tubes 2, by using sample distribution unit 3 and reagent injector unit 4 on the basis of predetermined information. More specifically, an undiluted reference liquid is supplied into first test tube 2a (FIG. 9A) by sample distribution unit 3. Next, a reagent is added by reagent injector unit 4 to dilute the reference liquid. The resultant liquid is used as reference liquid A, which serves to correct the characteristics of the electrodes. A test liquid, such as a blood serum, is supplied into second test tube 2b by sample distribution unit 3, and a reagent is added by reagent injector unit 4 to dilute the test liquid. The resultant liquid is used as test liquid B, which is to be analyzed. Likewise, an undiluted reference liquid is supplied into test tube 2c and is diluted with a reagent. The resultant liquid is used as reference liquid C, which serves to wash the electrodes. Reference liquid D, used for correcting the characteristics of the electrodes for the next sample of a test liquid, is supplied into test tube 2d. In this way, the liquid-supplying operation necessary for measurement of one sample of the test liquid is performed.

Figure 9A:
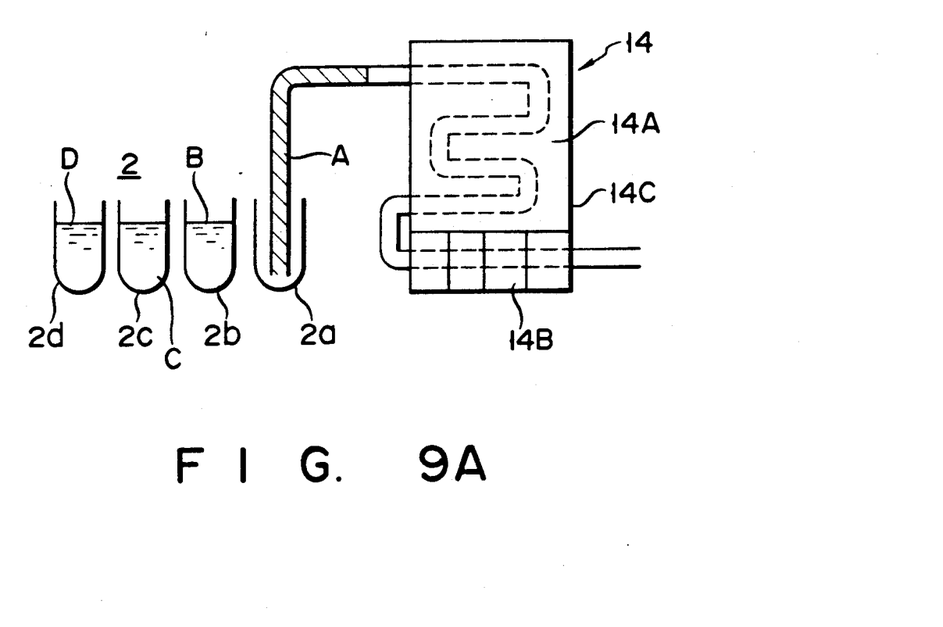
FIGS. 9A–9F are views for explaining the operation of the ion concentration measurement.
Figure 9B:
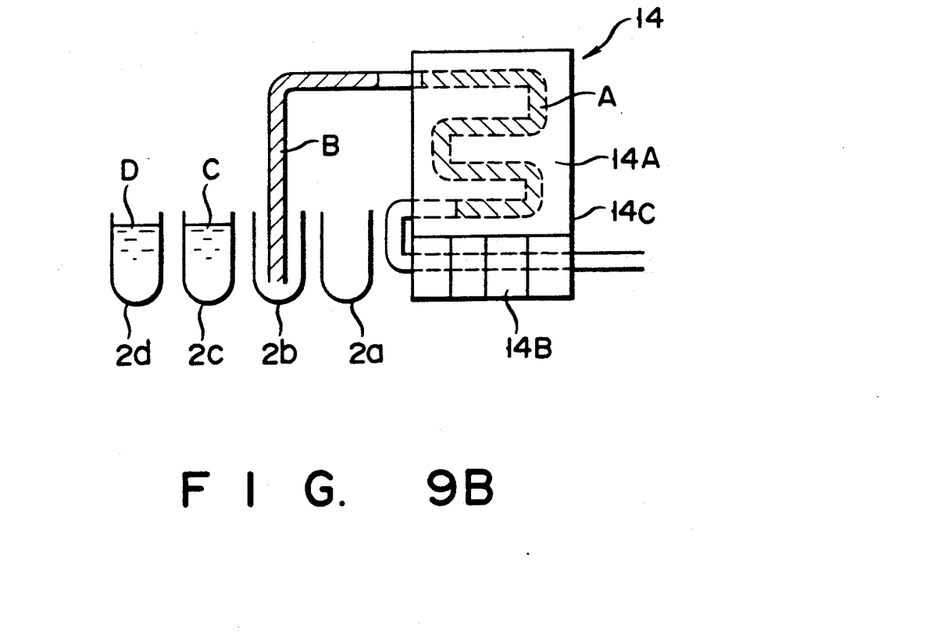
Figure 9C:
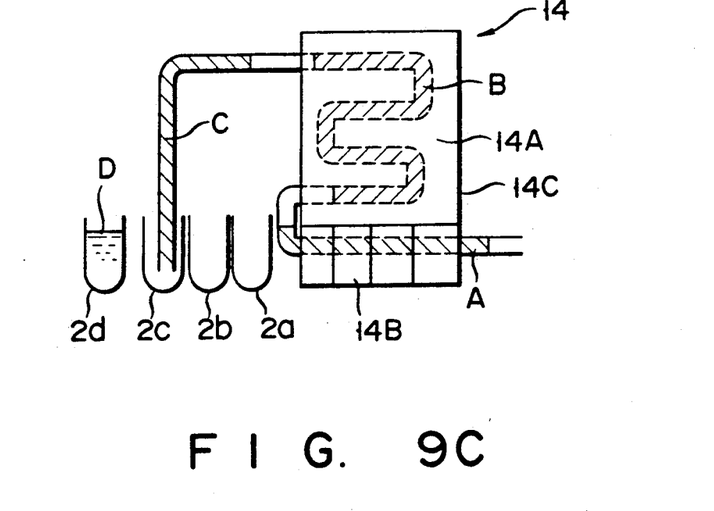
Figure 9D:
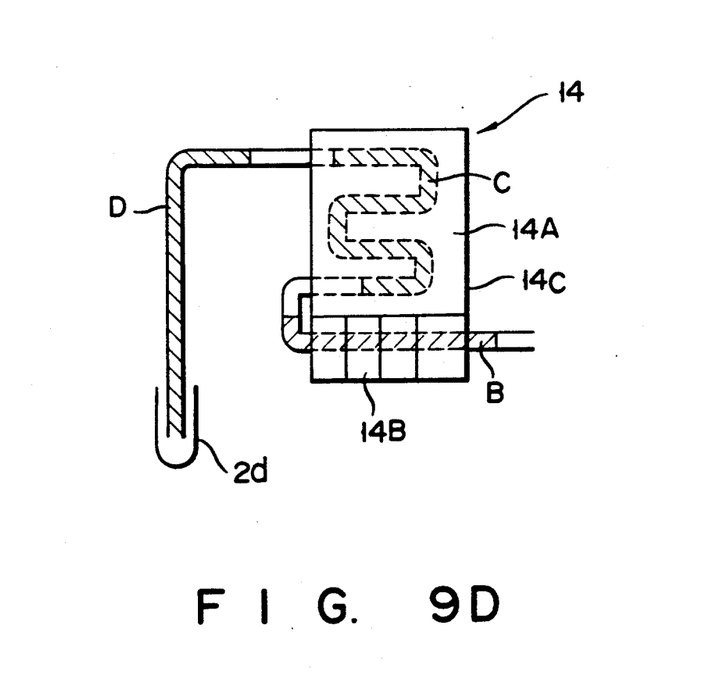
Figure 9E:
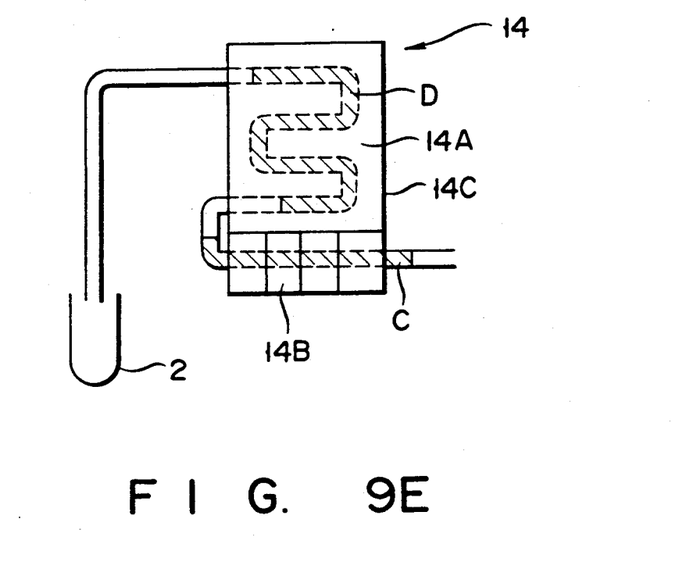
Figure 9F:
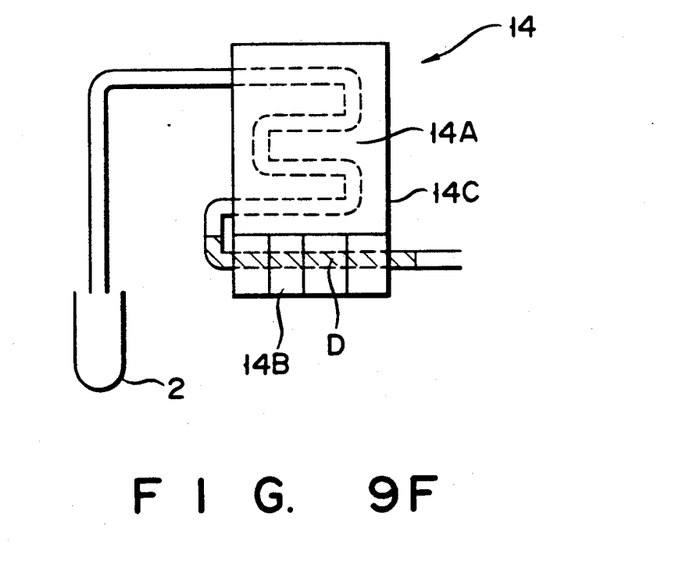

When test tubes 2a-2d are stopped under suction nozzle 11, this nozzle is driven by vertically movable mechanism 11a such that it successively sucks liquids from selected ones of test tubes 2. As is indicated by the oblique lines in FIG. 9A, reference liquid A is sucked from test tube 2a through suction nozzle 11 by use of suction pump 12. After a predetermined time (e.g., eighteen seconds), test liquid B is sucked from test tube 2b through suction nozzle 11, as indicated by the oblique lines in FIG. 9B. At this time, reference liquid A is stationary within heat block 14A and is heated such that its temperature is maintained at a constant value, e.g. 37° C. Reference liquid A corresponds to the reference liquid used before the measurement of sample SMP1 shown in FIG. 8. Eighteen seconds after this, reference liquid C is sucked from test tube 2c through suction nozzle 11, as is indicated by the oblique lines in FIG. 9C. At this time, diluted test liquid B enters heat block 14A and is heated such that its temperature is maintained at 37° C. Simultaneously, reference liquid A moves to electrode section 14B, in which the electromotive force of reference liquid A is measured. The measured electromotive force is electromotive force En described above. After a further eighteen seconds, reference liquid C enters heat block 14A by the action of suction pump 12, as shown in FIG. 9D. Reference liquid C is heated such that its temperature is maintained at 37° C. Diluted test liquid B moves to heat block 14B, so as to measure the electrolytes. Eighteen seconds after this, reference liquid C passes through electrode section 14B by the action of suction pump 12, thereby washing electrode section 14B, as shown in FIG. 9E. At this time, reference liquid D enters heat block 14A, and reference liquid D is heated such that its temperature is maintained at 37° C. By the next sucking action of suction pump 12, reference liquid D is moved to electrode section 14B, in which electromotive force $En+1$ is measured. In this fashion, the electromotive force measurement of one liquid is completed. In this way, the electromotive force of a reference liquid is calculated, using the formula mentioned above, and the electromotive force of the sample is detected on the basis of the calculation. Needless to say, the above embodiment is no more than one embodiment and does not limit the scope of the present invention.

Reference liquid A (which is used for the calibration of electrodes), diluted test liquid B, and reference liquid C (which is used for washing electrodes) are discharged from electrode section 14B. They are successively guided into drain tube 16 by the action of suction pump 12 after passing through three-way cock 15. Incidentally, the length of tube 13A, which is extends from suction nozzle 11 to electrode section 14B, is determined such that two samples can be handled, and all the operations mentioned above are performed under the control of a microcomputer.

The present invention is not limited to the embodiment mentioned above. It can be modified in various manners as long as the modifications do not depart from the spirit of the invention.

What is claimed is:

1. A method for measuring an ion concentration of a test liquid using an electrode device including a reference electrode, ion-selective electrodes and a liquid path through which a test liquid to be tested is passed for measuring electromotive forces generated between the reference electrode and the ion-selective electrodes, comprising the steps of:

conducting a reference liquid with a known ion concentration into the liquid path of the electrode device to measure a first electromotive force;

conducting a first standard liquid with a concentration having a value smaller than that of the reference liquid into the liquid path of the electrode device to measure a second electromotive force;

conducting the reference liquid with the known ion concentration into the liquid path of the electrode device to measure a third electromotive force after the measuring of the second electromotive force is performed;

obtaining a first mean value of the first and third electromotive forces of the reference liquid;

calculating a first electromotive force difference between the first mean value and the second electromotive force;

conducting the reference liquid with the known ion concentration into the liquid path of the electrode device to measure a fourth electromotive force;

conducting a second standard liquid with a known high ion concentration having a value larger than that of the reference liquid into the liquid path to measure a fifth electromotive force;

conducting the reference liquid with the known ion concentration into the liquid path to measure a sixth electromotive force after the measuring of the second standard liquid is performed;

obtaining a second mean value of the fourth and sixth electromotive forces of the reference liquid;

calculating a second electromotive force difference between the second mean value and the fifth electromotive force;

generating at calibration curve according to the first and second electromotive force differences;

conducting the reference liquid into the liquid path of the electrode device to measure a seventh electromotive force;

conducting the test liquid into the liquid path to measure an eighth electromotive force;

conducting the reference liquid into the liquid path of the electrode device to wash the liquid path after measurement of the eighth electromotive force of the test liquid is performed;

conducting the reference liquid into the liquid path to measure a ninth electromotive force after the liquid path is washed by the reference liquid;

obtaining an electromotive force of the reference liquid by weighting with constants the seventh and ninth electromotive forces of the reference liquid obtained before and after the measurement of the eighth electromotive force of the test liquid;

obtaining a third electromotive force difference between the eighth electromotive force of the test liquid and the weighted electromotive force of the reference liquid; and determining an unknown ion concentration of the test liquid by plotting the third electromotive force difference against the generated calibration curve.

2. A method according to claim 1, wherein the third difference electromotive force $\Delta Es$ is obtained by executing the following formula:

$$\Delta Es = Es - (K1 \cdot En + K2 \cdot En+1)/(K1+K2)$$

where Es represents the eighth electromotive force of the test liquid, En represents the seventh electromotive force measured before the measurement of the test liquid, $En+1$ represents the ninth electromotive force measured after the measurement of the test liquid, and K1 and K2 represent the constants determined experimentally.

3. A method according to claim 2, wherein values of the constants K1 and K2 are determined to be 0.5 and 0.5 or 1.0 and 1.0, respectively.

4. A method according to claim 1, which further comprises the steps of:

maintaining the temperature of the electrode device at a predetermined constant value; and setting the temperature of the reference liquid and the test liquid at the predetermined constant value before the reference and test liquids are conducted to the liquid path of the electrode device, respectively.

* * * * *